United States Patent
Guez et al.

(10) Patent No.: US 9,974,344 B2
(45) Date of Patent: May 22, 2018

(54) INJURY MITIGATION SYSTEM AND METHOD USING ADAPTIVE FALL AND COLLISION DETECTION

(71) Applicant: GraceFall, Inc., Narbeth, PA (US)

(72) Inventors: Allon Guez, Narbeth, PA (US); Helen Guez, Narbeth, PA (US)

(73) Assignee: GraceFall, Inc., Narbeth, PA (US)

( * ) Notice: Subject to any disclaimer, the term of this patent is extended or adjusted under 35 U.S.C. 154(b) by 0 days. days.

(21) Appl. No.: 15/269,820

(22) Filed: Sep. 19, 2016

(65) Prior Publication Data

US 2017/0006931 A1 Jan. 12, 2017

Related U.S. Application Data

(63) Continuation-in-part of application No. 15/208,399, filed on Jul. 12, 2016, now abandoned, which is a
(Continued)

(51) Int. Cl.
*A41D 13/018* (2006.01)
*A61B 5/0476* (2006.01)
(Continued)

(52) U.S. Cl.
CPC .............. *A41D 13/018* (2013.01); *A61B 3/14* (2013.01); *A61B 5/0476* (2013.01);
(Continued)

(58) Field of Classification Search
CPC .. A41D 13/018; A61B 5/0476; A61B 5/0488; A61B 65/6803; A61B 5/7203;
(Continued)

(56) References Cited

U.S. PATENT DOCUMENTS 6,219,578 B1 * 4/2001 Collins .............. A61N 1/36036
607/2
6,796,947 B2 9/2004 Watt et al.
(Continued)

FOREIGN PATENT DOCUMENTS

WO WO 2009/1158295 12/2009
WO WO 2013/1019844 2/2013

OTHER PUBLICATIONS

Gardner, Andrew B. et al."One Classs Novelty Detection for Seizure Analysis from Intracranial EEG". Journal of Machine Learning Research, pp. 1025-1044., Dec. 2006.
(Continued)

*Primary Examiner* — Thomas Alunkal
(74) *Attorney, Agent, or Firm* — DLA Piper LLP (US)

(57) ABSTRACT

A wearable safety device assembly is disclosed. The assembly includes at least one sensor configured to obtain one or more signals from a user. One of the at least one sensors comprises a vestibular (and startling/surprise related) motion sensor specially configured to obtain vestibular (and startling/surprise related) signals. Vestibular (and startling/surprise related) data indicative of a user's vestibular (and startling/surprise related) state is extracted from the one or more signals and used to determine whether a user is undergoing an event such as a fall or a startling movement. When it is determined that a user is undergoing an event, the processor of the wearable safety device transmits an activation signal to the safety device. Optionally, the processor may transmit data and information related to the vestibular (and startling/surprise related) system and recorded signals to a data repository.

22 Claims, 8 Drawing Sheets

Related U.S. Application Data continuation-in-part of application No. 14/520,385, filed on Oct. 22, 2014, now abandoned.

(60) Provisional application No. 61/895,589, filed on Oct. 25, 2013.

(51) Int. Cl.

| | | |
|---|---|---|
| *A61B 5/0488* | (2006.01) | |
| *A61B 3/14* | (2006.01) | |
| *G06N 99/00* | (2010.01) | |
| *G05B 11/01* | (2006.01) | |
| *A61B 5/00* | (2006.01) | |
| *A61B 5/04* | (2006.01) | |
| *A61B 3/113* | (2006.01) | |
| *A61B 5/0496* | (2006.01) | |
| *A61B 5/11* | (2006.01) | |

(52) U.S. Cl.
CPC ............ *A61B 5/0488* (2013.01); *G05B 11/01* (2013.01); *G06N 99/005* (2013.01); *A61B 3/113* (2013.01); *A61B 5/0075* (2013.01); *A61B 5/04012* (2013.01); *A61B 5/0496* (2013.01); *A61B 5/1117* (2013.01); *A61B 5/1128* (2013.01); *A61B 5/6803* (2013.01); *A61B 5/7203* (2013.01); *A61B 5/7282* (2013.01); *A61B 2562/0219* (2013.01)

(58) Field of Classification Search
CPC .............. A61B 5/04012; A61B 5/7282; G08B 21/0446; G08B 21/043
See application file for complete search history.

(56) References Cited

U.S. PATENT DOCUMENTS

| | | | |
|---|---|---|---|
| 7,017,195 | B2 | 3/2006 | Buckman et al. |
| 7,403,815 | B2 | 7/2008 | Katz et al. |
| 7,460,886 | B2 | 12/2008 | Mazzarolo |
| 7,541,934 | B2 | 6/2009 | Fredriksson et al. |
| 7,630,757 | B2 | 12/2009 | Dorfmeister et al. |
| 8,041,429 | B2 | 10/2011 | Kirby |
| 8,184,983 | B1 * | 5/2012 | Ho ............... H04B 11/00 345/156 |
| 8,355,788 | B2 | 1/2013 | Mechlenburg et al. |
| 8,396,570 | B2 | 3/2013 | Dadd et al. |
| 8,773,256 | B2 * | 7/2014 | Ten Kate ............ G08B 21/04 340/539.11 |
| 2004/0183283 | A1 | 9/2004 | Buckman |
| 2006/0206167 | A1 | 9/2006 | Flaherty |
| 2007/0038268 | A1 * | 2/2007 | Weinberg ............... A61H 3/00 607/62 |
| 2008/0079301 | A1 * | 4/2008 | Schaaf ................. A47C 7/14 297/313 |
| 2011/0230791 | A1 * | 9/2011 | Ten Kate ........... G08B 21/0446 600/595 |
| 2012/0083700 | A1 | 4/2012 | Osorio |
| 2012/0277835 | A1 * | 11/2012 | Della Santina ...... A61N 1/0526 607/62 |
| 2013/0023798 | A1 * | 1/2013 | Greene ............... A61B 5/6828 600/595 |
| 2013/0245714 | A1 | 9/2013 | Gupta et al. |
| 2014/0081346 | A1 * | 3/2014 | Eguibar ............... A61N 1/0526 607/45 |
| 2014/0163425 | A1 | 6/2014 | Tran |
| 2014/0276238 | A1 * | 9/2014 | Osorio ................. A61B 5/1117 600/595 |
| 2014/0330171 | A1 * | 11/2014 | Pan ..................... A61B 5/1117 600/595 |
| 2015/0039057 | A1 * | 2/2015 | Della Santina .... A61N 1/36032 607/62 |
| 2016/0183607 | A1 * | 6/2016 | Lopez Yunez ....... A41D 13/018 2/455 |

OTHER PUBLICATIONS

Kim, Youngm00 et al. "Neuro-imaging results for Rooney songs". Drexel University, pp. 312-314. Feb. 2006. (Submitted as three separate pages).

Kounios, John et al., "The Aha! Moment—The Cognitive Neuroscience of Insight". Current Directions in Physiological Science, pp. 210-216, Aug. 2009.

Schiller, Jeannine et al., "Fall Injury Episodes Among Noninstitutionalized Older Adults: United States, 2001-2003", Advance Data From Vital and Health Statistics. No. 392. Sep. 21, 2007.

* cited by examiner

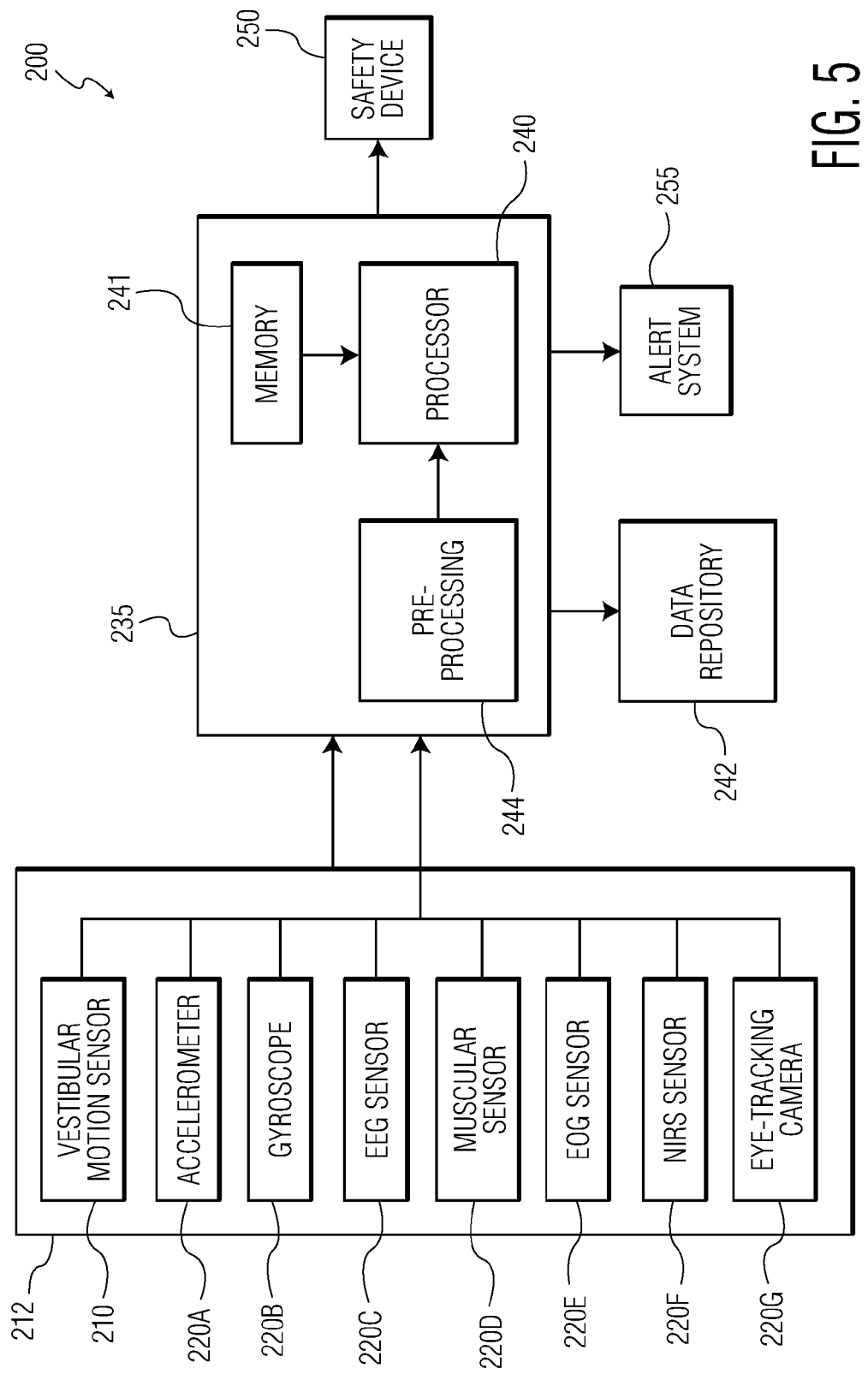

INJURY MITIGATION SYSTEM AND METHOD USING ADAPTIVE FALL AND COLLISION DETECTION

CROSS-REFERENCE TO RELATED APPLICATIONS

This application is a continuation-in-part of U.S. patent application Ser. No. 15/208,399, filed Jul. 12, 2016, which is a continuation-in-part of U.S. patent application Ser. No. 14/520,385, filed Oct. 22, 2014, which claims the benefit of the filing date of U.S. Provisional Application No. 61/895,589, filed Oct. 25, 2013, the teachings of all of which are incorporated herein by reference.

TECHNICAL FIELD

The present invention relates to a system for protecting a person from injuries that may otherwise be sustained by a fall, collision, or other bodily impact.

BACKGROUND

Many elderly tend to be prone to losing their balance and falling. Such falls result in breaks, fractures, and even mortalities. According to the Centers for Disease Control, the annualized rate of fall/collision injury episodes for adults, aged 65 years and over who were not institutionalized in 2001-2003, was 51 episodes per 1,000 people. Annually, one in three Americans over the age of 65 experiences a fall/collision and many of these falls/collisions are recurrent. Further, nearly 60% of older adults who experienced injuries due to falling visited an emergency room for treatment or advice.

EEG, NIRS, and other neural-imaging techniques are becoming more useful in being able to detect certain states of mind prior to the subject actually knowing how he or she feels. It is known that brain signals can be used to indicate a person's current activity state and to predict a change in the person's activity state. These techniques can be used for event detection (i.e., the early detection of falls, startling reflexes).

Prior art systems have discussed deploying personal safety devices based on event detection. For example, a number of prior art systems discuss approaches to deploying airbag systems for protecting a wearer during a fall or other accident. However the majority of prior art systems are aesthetically unpleasing which is directly correlated with reduced compliance in wearing the personal safety devices.

Additionally, prior art systems face problems associated with the timing and sensitivity of detecting falls. For example, the prior art systems may not be able to detect a fall/startling movement with confidence until there is not enough time to deploy a safety device to prevent injury during the fall/startling movement. This may be in part due to the fact that the prior art systems typically depend entirely on accelerometers or gyroscopes to detect and respond to movement. Signals obtained from the accelerometers or gyroscopes which indicate a fall/startling movement may be available only after the fall is already initiated and in progress. Accordingly, there may not be enough time after a fall is detected from signals obtained from the accelerometers or gyroscopes to deploy the safety device.

Prior art systems may also suffer from a high degree of sensitivity leading to a high number of false detections of falling events (i.e., false positives). This is due in part to prior art systems relying on information solely from gyroscopes and accelerometers. In signals acquired from gyroscopes and accelerometers intentional movements such as laughing, dancing, jumping, turns, and the like may have similar motion profiles as the motion profiles associated with unintended movement such as falls and startling effects. Accordingly, in prior art systems which solely utilized gyroscopes and accelerometers it would be impossible to distinguish between intentional and unintentional movements, leading to a high number of false positives.

Accordingly, it would be beneficial to provide a system and a method for detecting body signals indicative of an imminent fall and/or startling movement and activating a safety device to mitigate damage or injury resulting from the fall and/or startling movement. There is a need for faster and more accurate systems for detecting unintentional movements such as falls and/or startling movement. Furthermore, due to vast variations in the causes, pathologies and scenarios of falling and/or startling movements, such a system should be capable of adapting its performance to the specific and individual user.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention provides a system and a method for detecting body signals indicative of an event such as an imminent fall and/or a startling movement and activating a safety device to mitigate damage or injury resulting from the fall and/or startling movement. Notably, the system and method are capable of adapting its performance to the individual user. In particular, the body signals can be indicative of activity in the vestibular (and startling/surprise related) system discovered to provide timely and accurate information regarding an imminent fall and/or startling movement. Although the vestibular (and startling/surprise related) system is particularly sensitive to movement, it has long been the focus of stimulation techniques rather than motion detection as is used herein.

The systems and methods disclosed herein can be useful for users with neurological disorders (e.g., Parkinson's, epilepsy, Multiple Sclerosis), those who are aged, those who are currently experiencing or recovering from acute injury or illness, and the like.

An exemplary embodiment of the present invention includes methods and systems having at least one sensor configured to obtain one or more signals from a user, wherein the at least one sensor further comprises a vestibular (and startling/surprise related) sensor specially configured to obtain vestibular (and startling/surprise related) signals. The exemplary embodiment of the present invention also includes at least one processor electronically coupled to the at least one sensor and to a memory storing computer readable instructions which cause the processor receive the one or more signals from the at least one sensor, extract vestibular (and startling/surprise related) data indicative of a state of the user's vestibular (and startling/surprise related) system from the one or more signals, determine whether the user is undergoing an event by comparing the vestibular (and startling/surprise related) data to predetermined data, and transmit an activation signal to a safety device when it is determined that the user is undergoing the event. The methods and systems further include a safety device configured to deploy when the activation signal is received from the at least one processor.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

FIG. 5 shows a schematic drawing of a fall and collision detection and injury mitigation system using a vestibular (and startling/surprise related) motion sensor according to an exemplary embodiment of the present invention.

DETAILED DESCRIPTION

Figure 1:
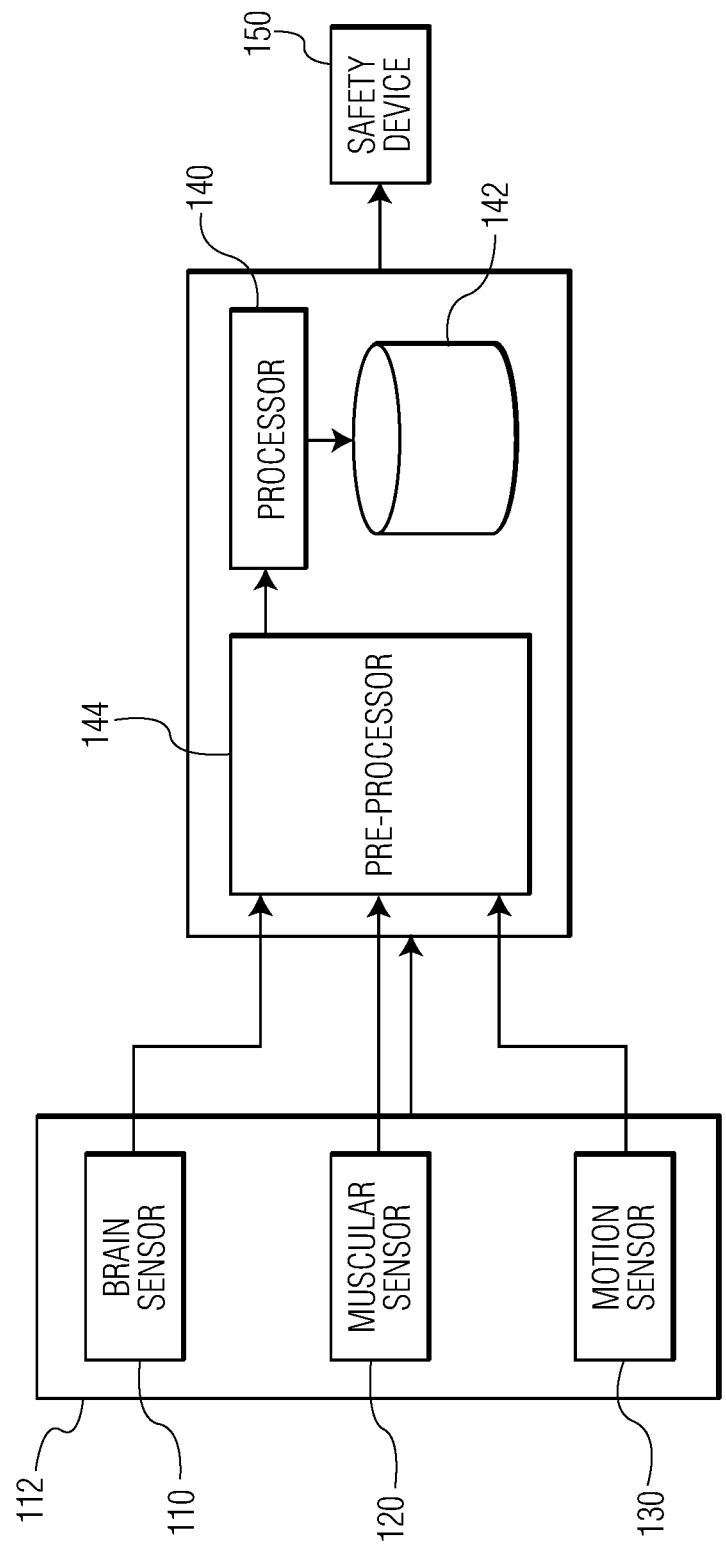
FIG. 1 shows a schematic drawing of a fall and collision detection and injury mitigation system according to an exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Although the subject matter described herein may be described in the context of illustrative implementations to process one or more computing application features/operations for a computing application having user-interactive components the subject matter is not limited to these particular embodiments. Rather, the techniques described herein can be applied to any suitable type of user-interactive component execution management methods, systems, platforms, and/or apparatus.

The present invention may be implemented as circuit-based processes, including possible implementation as a single integrated circuit (such as an ASIC or an FPGA), a multi-chip module, a single card, or a multi-card circuit pack. As would be apparent to one skilled in the art, various functions of circuit elements may also be implemented as processing blocks in a software program. Such software may be employed in, for example, a digital signal processor, micro-controller, or general-purpose computer.

The present invention can be embodied in the form of methods and apparatuses for practicing those methods. The present invention can also be embodied in the form of program code embodied in tangible media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium; etc., generated using a method and/or an apparatus of the present invention.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

Referring in general to the Figures, a fall and collision detection and injury mitigation system 100 ("system 100") according to an exemplary embodiment of the present invention is disclosed. System 100 uses physiological and movement data to anticipate when a person ("the user") wearing system 100 is in imminent danger or is in fact falling and activates an injury mitigation device to attempt to minimize potential injury from the fall or to prevent fall altogether.

System 100 is comprised of a plurality of sensors attached to the user that measure physiological and physical data and transmit that data to a processor, which in turn determines whether the data are indicative of an imminent fall. If so, the processor transmits an electronic signal to activate the injury mitigation device.

Referring specifically to FIG. 1, electronic schematic of system 100 is shown. System 100 includes a brain sensor 110 that is adapted to receive a first electrical signal and to transmit a first electronic signal based on the first electrical signal. In an exemplary embodiment, brain sensor 110 can be an electro-encephalocardiogram ("EEG") sensor, a near infrared sensor (NIRS), or other known or as yet unknown type of brain sensor. In an exemplary embodiment, brain sensor 110 can be attached (invasively or non-invasively based on the brain sensor type) to the user's forehead, skull, top of the neck or back of the head depending on the specific neural tissue such as, for example, the vestibular (and startling/surprise related) system, Central Nervous System or peripheral nervous system that is being tracked.

System 100 also includes a muscular sensor 120 that is adapted to receive a second electrical signal and to transmit a second electronic signal based on the second electrical signal. In an exemplary embodiment, muscular sensor can be an electromyography ("EMG") sensor, or other known or as yet unknown type of muscular sensor. In an exemplary embodiment, muscular sensor 120 can be attached to the user's thighs, picking up sensory information from quadriceps or hamstrings; upper arms; neck; or other muscle groups whose reflexive electrical activation is being pursued and monitored as related to vestibular (and startling/surprise) response.

System 100 also includes a movement sensor 130 that is adapted to sense movement and to transmit a third electronic signal based on the movement. In an exemplary embodiment, movement sensor 130 can be an accelerometer, gyro or other known or as yet unknown type of velocity, displacement, acceleration, jerk or other movement sensor. In an exemplary embodiment, movement sensor 130 can be attached to the user's chest. Sensor 130, however, may be located anywhere on the user's core and head, depending on the product design, convenience, and other potential user disabilities.

While FIG. 1 shows brain sensor 110, muscular sensor 120, and movement sensor 130 as three separate sensors, in an exemplary embodiment, brain sensor 110, muscular sensor 120, and movement sensor 130 can be provided as a single unit 112 that needs only to be attached to a single location on the user. An exemplary location for single unit 112 can be on the back of the user's neck. In this location, brain sensor 110, is able to sense neurological signals generated by the vestibular nuclei, on either side of the brain stem. Muscular sensor 120 can alternatively be used to sense movement of the trapezius and sternocleidomastoid muscles of the neck and movement sensor 130 can sense movement of the user's body.

A processor 140 is electronically coupled to brain signal sensor 110, muscular signal sensor 120, and movement sensor 130. Processor 140 is configured to process the first electronic signal, the second electronic signal, and the third electronic signal and generate a result. Processor 140 can be an electronic microprocessor and is powered by an electrical power source, such as a battery (not shown).

Processor 140 can include a memory 142 for data storage to store pluralities of the first electronic signal, the second electronic signal, and the third electronic signal. A signal preprocessor 144 can optionally be provided to preprocess the electrical signals received from brain signal sensor 110, muscular signal sensor 120, and movement sensor 130. Processor 140 computes with a plurality of signal processing algorithms, either available in public domain (machine learning, pattern recognition, neural-networks, adaptive control, filtering, online optimization and many other well-known or yet-to-be-developed techniques) or customized by the designer to accommodate desired operation of system 100. Processor 140 also implements training/adaptation/customization algorithms in order to adjust for the expected variations in the required alarm threshold and proper activation of the safety device for each user.

Figure 2:
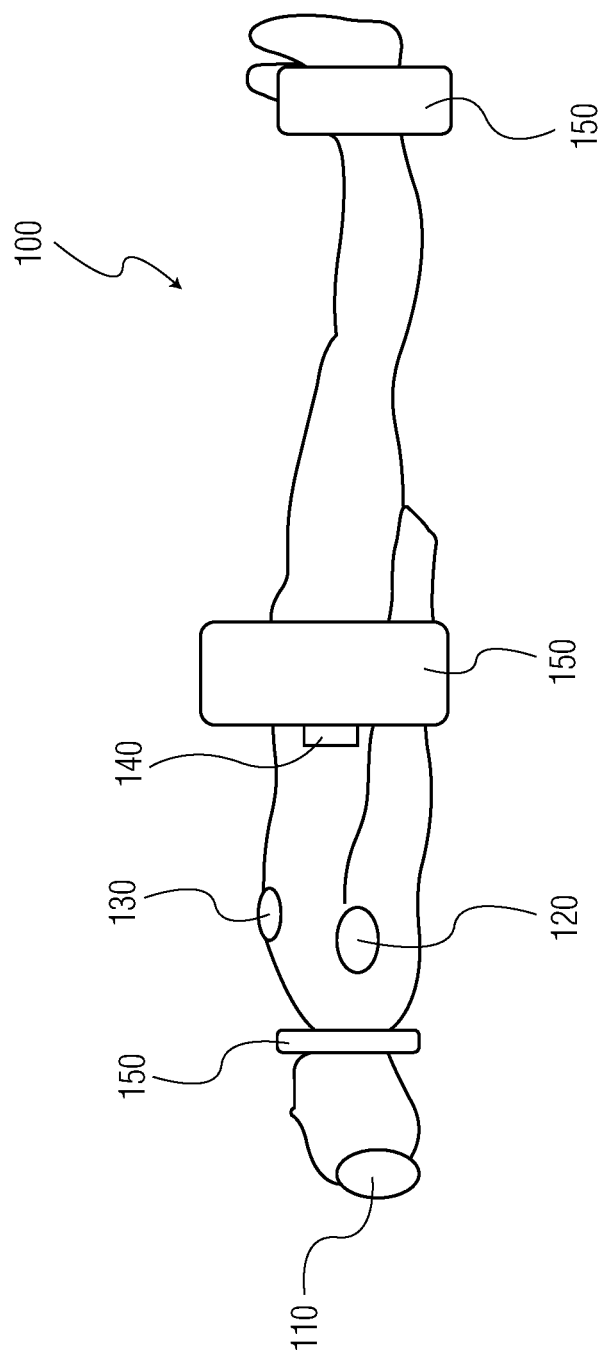
FIG. 2 shows a deployable airbag that can be used with the fall and collision detection and injury mitigation system of FIGS. 1 and 5.

A safety device 150 is electronically coupled to processor 140 such that, when the result meets a predetermined threshold value as determined by the software/hardware-based algorithms, safety device 150 is activated. As shown in FIG. 2, safety device 150 can be a deployable airbag 152 or a plurality of airbags 152. Airbag 152 can be worn about the user's waist, neck/collar, and/or ankles and can be secured to the user by a releasable securing mechanism, such as, for example, a hook and loop attachment. An exemplary airbag that can be used with the present invention is disclosed in U.S. Pat. No. 7,017,195 to Bachman et al., which is incorporated herein by reference. Safety device 150 can be a disposable, for one time use or a multiple usage system.

Figure 3:
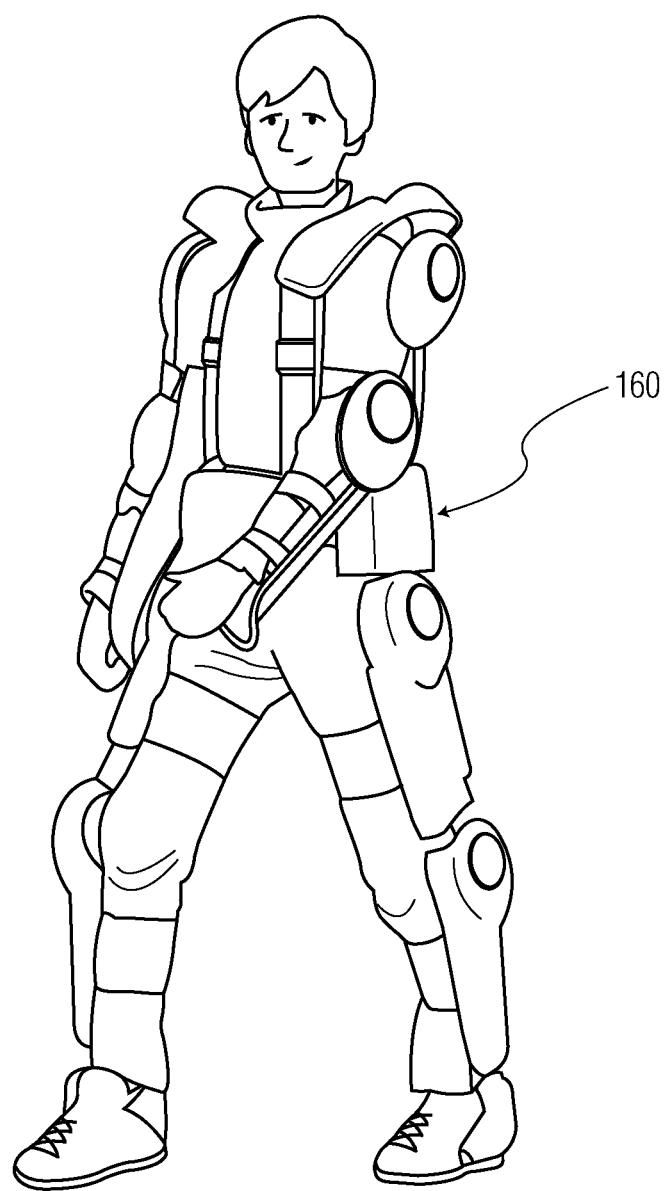
FIG. 3 shows an exoskeleton that can be used with the fall and collision detection and injury mitigation system of FIGS. 1 and 5.

Alternatively, safety device 150 can be another type of safety device, such as, for example, an exoskeleton 160, shown FIG. 3. Exoskeleton 160 can be worn by the user and can be activated to become rigid to prevent the user from falling upon determination by processor 140 that the user has imminent likelihood of falling. Safety device 150 can be disposable, for one time use or a multiple usage system.

System 100 can be triggered to activate when the user experiences different sensations. For example, system 100 can activate when the user senses an impending fall and actually begins to fall. Alternatively, system 100 can activate when the user faints or passes out (having no sense of an impending fall), and actually begins to fall. It can also detect changes in the motion, gait and postural stability patterns over time.

Prior to a user initiating use of system 100, it may be desirable for the user to "train" system 100 with regard to typical movements of user that may be associated with particular brain and or muscular signals. For example, user can be connected to system 100 and blindfolded or immersed in a virtual reality system, such as, for example, developed by Oculus VR, LLC, located in Irvine, Calif. The user can then be provided with the sensation of falling while recording brain activity with brain signal sensor 100, muscle activity with muscular signal sensor 120 and movement with movement sensor 130. This process can be repeated a plurality of times. Processor 140 determines brain and muscular signals associated with the user sensing and reacting to an impending fall and uses the values of such signals to determine threshold values for activating safety device 150. Thus, processor 140 also implements training/adaptation/customization algorithms in order to adjust for the expected variations in the required alarm threshold and proper activation of the safety device per each user.

In operation, using system 100 with brain signal sensor 110, muscular signal sensor 120, and movement sensor 130 attached to the user, when the user is about to fall, brain signal sensor 110 receives a first electrical signal from the brain, indicating a significant increase in brain activity, resulting from the user realizing that he/she is about to fall. Brain signal sensor 110 generates a first electronic signal based on the first electrical signal and transmits the first electronic signal to processor 140.

Within a first, short period of time of the user's brain generating the first electrical signal, such as, for example, within a range of about 50 to about 200 ms, muscular signal sensor 120 receives a second electrical signal from the user's musculature, indicating a sudden contraction of muscles to brace the user for the impending fall, such signal may be received for example, within the range of between about 100 to about 800 ms. If such muscular activity is present, muscular signal sensor 120 generates a second electronic signal based on the second electrical signal and transmits the second electronic signal to processor 140. If such a movement is experienced, movement sensor 130 receives a movement sensation from the user, indicating the likely start of the fall. Movement sensor 130 generates a third electronic signal based on the movement sensation and transmits the third electronic signal to processor 140.

Processor 140 processes the first electronic signal, the second electronic signal, and the third electronic signal to generate a result and transmits an activation signal to safety device 150 if the data as processed by the algorithms warrants that the result meets an activation decision value. The activation signal activates safety device 150 to mitigate damage and/or injury to the user when the user falls.

Alternatively, if the user faints or otherwise loses consciousness and falls due to his/her loss of consciousness, system 100 can activate safety device 150 based on a different set of parameters. In such a situation, brain signal sensor 110 receives a first electrical signal from the brain, indicating a significant decrease in brain activity, resulting from the user losing consciousness. Brain signal sensor 110 generates a first electronic signal based on the first electrical signal and transmits the first electronic signal to processor 140.

Within a first, short period of time of the user's brain generating the first electrical signal, muscular signal sensor 120 receives a second electrical signal from the user's musculature, indicating a sudden change of activation of muscles, also due to loss of consciousness. Muscular signal sensor 120 generates a second electronic signal based on the second electrical signal and transmits the second electronic signal to processor 140. Within a second, short period of time of the musculature generating the second electrical signal, movement sensor 130 receives a movement sensation from the user, indicating the start of the fall. Movement sensor 130 generates a third electronic signal based on the movement sensation and transmits the third electronic signal to processor 140.

Processor 140 processes the first electronic signal, the second electronic signal, and the third electronic signal to generate a result and transmits an activation signal to safety device 150 if the data as processed by the algorithms warrants that the result meets a threshold value. The activation signal activates safety device 150 to mitigate damage and/or injury to the user when the user falls.

Therefore, by way of example only, if the first electrical signal from the brain that is received by brain signal sensor 110 is above a first brain signal threshold level, and if the second electrical signal received from the musculature that is received by muscular signal sensor 120 is above a first musculature signal threshold level, processor 140 interprets those signals as the user realizing that he/she is about to fall and waits for movement sensor 130 to determine that the user is actually falling before transmitting the signal to activate safety device 150.

Alternatively, if the first electrical signal from the brain that is received by brain signal sensor 110 is below a second brain signal threshold level, less than the first brain signal threshold level, and if the second electrical signal received from the musculature that is received by muscular signal sensor 120 is below a second musculature signal threshold level, less than the first muscular signal threshold level, processor, 140 interprets those signals as the user fainting and waits for movement sensor 130 to determine that the user is actually falling before transmitting the signal to activate safety device 150.

While system 100 is described above as requiring activation of brain signal sensor 110, muscular signal sensor 120, and movement sensor 130 in a specific order in order to activate safety device 150, the present invention also contemplates a multiplicity of activation decision patterns and algorithms which are based on signals from the brain signal sensor 110, muscular signal sensor 120, and movement sensor 130 in a variety of methods including different time sequential order, as well as the activation of only one or two of brain signal sensor 110, muscular signal sensor 120, and movement sensor 130 in order to activate safety device 150.

Additionally, instead of requiring specific timing or sequence of activation of brain signal sensor 110, muscular signal sensor 120, and movement sensor 130, in order to activate safety device 150, those skilled in the art will recognize that other known types of mechanisms and techniques, such as, for example, machine learning, pattern recognition, neural networks, adaptive control, filtering, and—line optimization can be used to determine whether the user is sensing an impending and/or actual fall and activate safety device 150.

System 100 also has the ability to "learn" the user and recalibrate the threshold values for activation of safety device 150 based on the user and the user's daily activities. For example, of the first electronic signal exceeds the value that would otherwise indicate that the brain may be sensing an impending fall, but neither the second nor the third electronic signal exceeds the values that would otherwise indicate that the musculature may be sensing an impending fall, or movement of the body indicates an actual fall, the threshold value of the first electronic signal may be raised. Similarly, the activation decision parameters such as the threshold values for either/both the second and third electronic signals, respectively, can be recalibrated if the remaining electronic signals do not indicate an impending fall.

Figure 4:
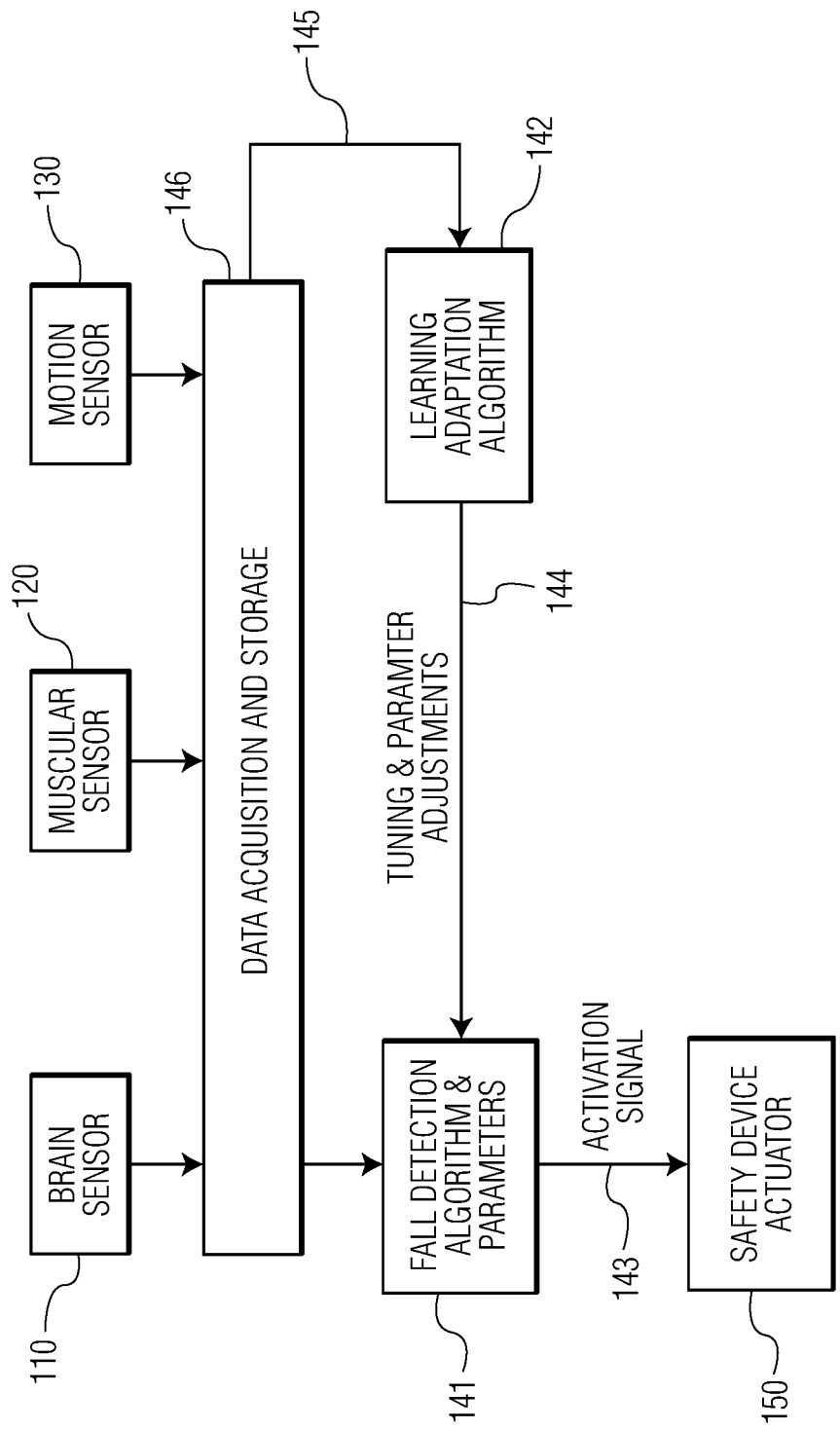
FIG. 4 is a flowchart describing an exemplary signal and information flow as well as exemplary modules for providing adaptation and tuning capabilities of the system for individual users.

A flowchart 400 describing an exemplary arrangement and operation implementing the "learning"/adaptation of system to a specific user is shown in FIG. 4. Module 141 provides the currently operational fall detection algorithm and parameters; module 142 is a learning adaptation algorithm; module 143 is an actual activation signal; module 144 is a tuning and parameter adjustment signal; module 145 is the access to historical measurements data for learning; and module 146 is data acquisition and storage.

An exemplary method of adaptation occurs as follows. Module 142 constantly monitors correlation between the actual activation 143 and the sensory data in 146 received by brain sensor 110, muscular sensor 120, and motion sensor 130 and adjusts the parameters in 141 whenever a "mismatch" is present, meaning that, whenever activation signal 141 activates safety device 150 but no falls occurred, or alternatively, when a fall occurs with safety device 150 not being activated. Common gradient descent, least square estimation, adaptive control, machine learning and other known adaptive signal processing techniques may be employed for such adjusting.

FIGS. 5-8 correspond to exemplary embodiments of the invention using one or more sensors including a vestibular (and startling/surprise related) motion sensor.

FIG. 5 illustrates a schematic drawing of an event detection system using a vestibular (and startling/surprise related) motion sensor according to an exemplary embodiment of the present invention. In particular, the event detection system may include at least one sensor is configured to obtain one or more signals from a user. The at least one sensor may include a vestibular (and startling/surprise related) motion sensor 210. The vestibular (and startling/surprise related) motion sensor 210 can be specially configured to include dedicated electroencephalogram (EEG), electromyography (EMG), electrooculography (EOG) and/or near infrared spectroscopy (NIRS) components configured to obtain signals from the user which are indicative of the state of the user's vestibular (and startling/surprise related) system. The specially configured and dedicated sensors may be specially configured to obtain vestibular (and startling/surprise related) signals. Vestibular (and startling/surprise related) signals include any signal pattern obtained from the user which indicates the state of the user's vestibular (and startling/surprise related) system.

Specialized EEG, EMG, EOG, NIR sensors and the like may obtain and extract vestibular and startling/surprise related signals within 200-300 milliseconds of the onset of body motion. The specialized EEG, EMG, EOG, NIRS sensors and the like may be specially configured to improve signal to noise ratios. The vestibular and startling/surprise related sensors may be located at the vicinity of the vestibular nerves (i.e., behind the ears), near the Vestibular Occular Reflex (VOR) zone (i.e., near eye muscles) and on the skin in places associated with the main muscle groups involved in the Vestibular Spine Reflex (VSR). Such areas which are not covered with hair and are smooth skin also enable cleaner signals with patch like sensors.

The vestibular (and startling/surprise related) system includes central projections which participant in three major classes of reflexes: (1) maintaining equilibrium and gaze during movement, (2) maintaining posture, and (3) maintaining muscle tone. As will be discussed below, observing the vestibular (and startling/surprise related) system may provide an indication of whether a movement is intentional or unintentional. The event detection system provides means for detecting events such as unintentional movement (i.e., fall or startling movement). As discussed in Vestibular system. (2016, Jul. 30). In *Wikipedia, The Free Encyclopedia*. Retrieved from https://en.wikipedia.org/w/index.php?title=Vestibular_system&oldid=732255945, incorporated herein by reference, the vestibular afferent signals are generated in both active (planned) and passive (unplanned/surprising) movements while the efferent signals descending to activate muscles groups in VOR and VSR are suppressed by top-down signals from other cortical areas anticipating such motion and preventing the reflexive action.

The first of the reflexes mediated by the vestibular (and startling/surprise related) system is the vestibule-ocular reflex (VOR). The VOR helps coordinate the head and eye movements necessary to keep a user's gaze fixated on objects of interest during movements of the head. For example, consider the horizontal movement of the eyes to the right. This movement requires contraction of the left medial and right lateral rectus muscles. Vestibular (and startling/surprise related) nerve fibers originating in the left horizontal semicircular canal project to the medial and lateral vestibular (and startling/surprise related) nuclei. Excitatory fibers from the medial vestibular (and startling/surprise related) nucleus cross to the contralateral abducens nucleus, which has two outputs. One of these outputs is a motor pathway that causes the lateral rectus of the right eye to contract; the other output is an excitatory projection that crosses the midline and ascends via the medial longitudinal fasciculus to the left oculomotor nucleus, where it activates neurons that cause the medial rectus of the left eye to contract. Finally, inhibitory neurons project from the medial vestibular nucleus to the left abducens nucleus, directly causing the motor drive on the lateral rectus of the left eye to decrease and also indirectly causing the right medial rectus to relax. Sensing activation of the VOR by sensing any of the outputs, excitations and inhibitions discussed above will aid in the early detection of motion.

The second of the reflexes mediated by the vestibular system is essential for postural adjustments of the head and includes the vestibulo-collic reflex (VCR). The VCR is a mechanism for controlling neck muscles to control for the head's orientation. The anatomical substrate for the VCR involves the medial vestibular nucleus. Axons from the medial vestibular nucleus descend in the medial longitudinal fasciculus to reach the upper cervical levels of the spinal cord. This pathway regulates head position by reflex activity of neck muscles. The pathway is activated in response to stimulation of the semicircular canals from rotational accelerations of the head. Accordingly, sensing the activation of the VCR can aid in the early detection of motion.

The third of theses reflexes mediated by the vestibular system is the vestibulo-spinal reflex (VSR) of the body. The VSR is a mechanism for altering the muscle tone, extension and position of the limbs and head with the goal of supporting posture and maintaining balance of the body and head. The anatomical substrate for the VSR for the body is mediated by a combination of pathways, including the lateral and medial vestibulospinal tracts and the reticulospinal tract. The inputs from the otolith organs project mainly to the lateral vestibular nucleus, which in turn sends axons in the lateral vestibulospinal tract to the spinal cord. The VSR is an assemblage of several reflexes named according to the timing (dynamic vs. static or tonic) and sensory input (canal, otolith or both). While terminology varies among authors, the term VSR usually also implies motor output to skeletal muscle below the neck, or in other words, it excludes the neck reflex which is called the VCR (discussed above).

For an example of the role of the VSR, consider the sequence of events involved in generating a labyrinthine reflex. When the head is tilted (rolled) to one side, both the canals and otoliths are stimulated, the vestibular nerve and vestibular nucleus are activated and impulses are transmitted via the lateral and medial vestibulospinal tracts to the spinal cord. This results in the induction of muscle activity. For example, extensor activity is induced on the side to which the head is inclined and flexor activity is induced on the opposite side.

Indeed, when the body is pitched, extensor tone changes according to the position of the head with respect to horizontal. Extensor tone is maximal when the angle of the head is 45 degrees with respect to horizontal (i.e. head is nose up as well as an additional 45 degrees towards upright). Extensor tone is minimal when the head is nose-down and pointing an additional 45 degrees down. There is also a "righting reflex". When the position of the head or body changes, reflex movements occur that tend to return the head or body to the normal posture. Accordingly, sensing activation of the VSR will therefore aid in the early detection of motion.

Accordingly, the at least one sensor 212 may include a vestibular (and startling/surprise related) motion sensor 210 having one or more specialized EEG, EMG, EOG, NIRS sensors and the like configured to obtain vestibular (and startling/surprise related) signals, including vestibular (and startling/surprise related) signals indicative of the three reflexes discussed above (i.e., the VOR, the VCR and the VSR). Each of the dedicated EEG, EMG, EOG, and/or NIRS sensors of the vestibular (and startling/surprise related) motion sensor may be specially configured to obtain vestibular (and startling/surprise related) signals. The sensors may be specially configured so that they can obtain the vestibular (and startling/surprise related) signals such as those present in the vestibulocochlear nerve (cranial nerve VIII). Obtaining vestibular (and startling/surprise related) signals from the vestibulocochlear nerve is difficult as the vestibulocochlear nerve is located deep within the skull. Thus, the dedicated EEG, EMG, EOG, and/or NIRS sensors of the specially configured vestibular (and startling/surprise related) sensor may be specially configured and positioned so that they may obtain vestibular (and startling/surprise related) signals. In particular, the dedicated vestibular (and startling/surprise related) may be placed in the vicinity of the vestibular nerves (i.e., behind the ears), near the Vestibular Occular Reflex (VOR) zone (i.e., near eye muscles) and on the skin close to main muscle groups associated with Vestibular Spine Reflex (VSR). Areas that are not covered with hair and are smooth skin may be preferred so that cleaner signals are obtained. In one embodiment the dedicated EEG sensors may include high-density mobile EEG sensors miniaturized for optimal placement of an electrode array to obtain vestibular (and startling/surprise related) signals. For example, the EEG sensors can be placed into glasses, a hearing aid, and the like. Similarly, the volitional muscle activity (VEMG) may be obtained by the dedicated EMG sensors of the vestibular (and startling/surprise related) sensor that are configured to record from surface electrodes placed over the tonically-activated sternocleidomastoid (SCM) muscles. In particular, the dedicated EMG sensors may include a noninverting surface electrode which is placed at the middle third of the sternocleidomastoid muscles, an inverting electrode placed at the sternoclavicular junction, and a ground electrode placed on the forehead. Vestibular (and startling/surprise related) signals can also be recorded from the extraocular muscles using surface electrodes placed near (approximately inferior to) the eyes. The surface electrodes may obtain vestibular (and startling/surprise related) signals including the ocular vestibular (and startling/surprise related) evoked myogenic potential (oVEMP) which is a manifestation of the VOR. The vestibular (and startling/surprise related) signal obtained by this method is particularly strong during up-gaze when the inferior oblique muscle is activated. In an alternative embodiment, instead of using surface electrodes, the oVEMP can be obtained by eye-tracking by one or more cameras and/or electrooculography (EOG).

In an exemplary embodiment of the invention the vestibular (and startling/surprise related) motion sensor 210 can be configured to sense volitional muscle activity data (VEMG) activity including vestibular (and startling/surprise related) evoked myogenic potential (VEMP).

The system of FIG. 5 may also include one or more additional sensors such as an accelerometer 220A, gyroscope 220B, an EEG sensor 220C, an muscular sensor 220D, an EOG sensor 220E, a near-infrared spectroscopy (NIRS) sensory 220F, and an eye-tracking camera 220G. The sensors 220A-220G may obtain signals indicative of brain and muscle activity which are not limited to vestibular (and startling/surprise related) signals.

As illustrated in FIG. 5 the one or more sensors may include an accelerometer 220A. The accelerometer 220A may be a micro-machined piezoresistive accelerometer similar to those currently used in various industrial applications. The configuration of the cantilever structures in piezoresistive accelerometers is similar to those in capacitive accelerometers, while their electrical measuring mechanisms are different. In piezoresistive accelerometers, a piezoresistor is often patterned on a thin suspending cantilever which connects the proof mass and the supporting frame. Due to the mechanical flexibility of the cantilever, a large mechanical strain occurs as the external acceleration displaces the proof mass. The strain is derived from the electrical resistance change in the piezoresistor.

Piezoresistive accelerometers can be fabricated by both surface micromachining and bulk micromachining. By using a piezoresistor as the sensing component, this type of accelerometers is advantageous due to the relatively simple configuration and fabrication. However, piezoresistive accelerometers are highly vulnerable to the temperature variation. Improved designs include the use of a large proof mass, integration with a temperature compensation circuitry, and the monolithic implementation with CMOS electronics.

Piezoelectric accelerometers have similar configuration to their piezoresistive counterparts, but measure the acceleration from the electrical voltage induced by the mechanical displacement of the cantilever. A notable difference is that piezoelectric accelerometers only respond to dynamic signals while the piezoresistive sensors can measure displacements under low and zero frequencies. Either type of accelerometer may be used in connection with an exemplary embodiment of the device.

Alternatively, the accelerometer 220A may include tunneling accelerometers. Tunneling accelerometers take advantage of the phenomenon that occurs when a conductive sharp tip and a counter electrode are positioned at a small gap distance on the order of 10 Å. Such accelerometers may be miniaturized for use in measuring vestibular (and startling/surprise related) signals such as VEMP. The tunneling accelerators can be mounted in a hearing aid (see FIGS. 6A and 6B), in glasses (see FIG. 7), in an implantable sensor, on a safety device (see FIG. 8), on an external surface of the body (e.g., the skin), or the like. In one embodiment where the accelerometer 220A is implantable and the temperature resistance of the piezoelectric accelerometers may provide additional movement information.

The one or more sensors may also include a gyroscope 220B, a sensor configured to measure the rotary rate of an object. In one embodiment, the gyroscope 220B can include micro-gyroscopes which utilize the Coriolis effect to convert the rotary motion of the subject into a measurable linear motion. The Coriolis effect refers to the generation of an imaginary force (Coriolis force) perpendicular to the moving direction of the subject within a rotating coordinate system. The rotary rate can therefore be determined using the above described sensing mechanisms of measuring linear accelerations. The gyroscope 220B sensor is especially well-suited to use in the embodiments of the system illustrated in FIGS. 6A and 7B which include devices resembling a hearing aid.

The one or more sensors may also include an EEG sensor 220C. The use of EEG systems to produce electrooculographic (and electronystagmography) data indicative of motion information including vestibular (and startling/surprise related) functioning has been described (see, e.g., Toglia, *Clin. Electroencephalogr*, October; 19(4):225-30 (1988)), the contents of which are incorporated herein by reference). However, it wasn't until 2009 that EEG data acquisition was demonstrated in a moving patient, and then only in persons moving linearly (see, e.g., Nolan, et al., *Proceedings of the 4th International IEEE EMBS Conference on Neural Engineering*, Antalya, Turkey, Apr. 29-May 2, 2009). Recently developed systems equipped with actively shielded electrodes and cables have been particularly designed to record electrophysiological data from moving and even walking probands (Waveguard™, ANT, Netherlands). Furthermore, advances in data analysis techniques permit improved cleaning of EEG signals from artifacts, instead of excluding such recordings (see, e.g., Gwin et al., *J. Neurophysiol.*, 103:3526-3534 (2010)). The development of high-density mobile EEG allows for adaptation of EEG paradigms to mobile applications. Accordingly, in one embodiment, while the vestibular (and startling/surprise related) motion sensors 210 may include specially configured high-density mobile EEG sensors configured to obtain, process and transmit one or more vestibular (and startling/surprise related) signals, other EEG sensors 220C may be used in addition to the EEG sensors specially configured for obtaining vestibular (and startling/surprise related) signals. The EEG sensors 220C can include one or more leads in contact with the user's scalp.

The one or more sensors may also include a muscular sensor 220D. The muscular sensor 220D may be adapted to receive or obtain an electrical signal indicative of muscle activity. The muscular sensor 220D can include a processor configured to convert the obtained or received electrical signal into an electronic signal. Alternatively the conversion from an electrical signal to an electronic signal can occur at pre-processing 244 or by the one or more processors 240. The muscular sensor 220D can transmit the electrical (or electronic) signal to the one or more processors 240. In an exemplary embodiment, the muscular sensor 220D can include an electromyography ("EMG") sensor. In an exemplary embodiment, the muscular sensor 220D can be attached to the user's thighs, picking up sensory information from quadriceps or hamstrings; upper arms; neck; or other major muscle groups whose reflexive electrical activation is being pursued and monitored. Optionally, the muscular sensor 220D can be utilized through connection (implanted, partially implanted, or on the skin) to one or more major muscle masses in the body. Such a muscular sensor 220D can be employed to provide one or more electrical signals configured to confirm motion detected via the vestibular (and startling/surprise related) motion sensor 210.

The one or more sensors may also include a sensor configured for electrooculagraphy (EOG). The EOG sensor 220E may be configured to record electrical signals proximate the eyes. The electrooculogram obtained by the EOG sensor may be used to determine eye movement which may be indicative of body movement.

The one or more sensors may also include a near-infrared spectroscopy (NIRS) sensor 220F. The NIRS sensors 220F may include wearable modules which are configured to communicate with a smartphone or tablet as a receiver such as those made by Alps Electronics, Ltd. A fully wireless NIRS device is also described by Achigui, et al., *Microelectronics Journal*, 39(10):Pages 1209-1217 (2008), incorporated herein by reference. In one embodiment, the NIRS sensor 220F makes use of dynamic threshold transistors (DTMOS) for low voltage (1V), low power and low noise enhancement. The design is composed of a transimpedance amplifier (TIA) and an operational transconductance amplifier (OTA). The OTA differential input pairs use DTMOS devices for input common mode range enhancement. The OTA is fabricated in a standard 0.18 μm CMOS process technology. Measurements under a 5 pF capacitive load for the OTA gives a DC open loop gain of 67 dB, unity frequency gain bandwidth of 400 kHz, input and output swings of 0.58 and 0.7 V, a power consumption of 18 μW, and an input referred noise of 134 nV/√Hz at 1 kHz without any extra noise reduction techniques.

The one or more sensors of the device may also include an eye-tracking camera 220G. The eye-tracking camera 220G may be configured to track eye movements indicative of intentional and unintentional movements.

Each of the one or more sensors, including the specially configured vestibular (and startling/surprise related) motion sensor 210 and the remaining sensors (accelerometer 220A, gyroscope 220B, an EEG sensor 220C, an muscular sensor 220D, an EOG sensor 220E, a near-infrared spectroscopy (NIRS) sensory 220F, and an eye-tracking camera 220G, discussed above) may be in communication with each other. Alternatively, the one or more sensors may operate independently of each other. Although FIG. 5 illustrates and embodiment having seven sensors, any combination of sensors, including those with fewer or greater number of sensors may be used. As discussed, the system 200 can also include one or more sensors 220A-220G configured to detect movement and adapted to receive or obtain an electrical signal indicative of movement. The one or more sensors 220A-220G can include a processor configured to convert the obtained or received electrical signal into an electronic signal. Alternatively, the conversion from an electrical signal to an electronic signal can occur at pre-processing 244 or by the one or more processors 240. The one or more sensors 220A-220G can transmit the electrical (or electronic) signal to the one or more processors 240. The one or more sensors can include one or more of an accelerometer, a gyroscope and other known or as yet unknown velocity, displacement, acceleration, jerk or other movement sensors. In an exemplary embodiment, the one or more sensors can be attached to the user's chest, or may also be incorporated into a hearing aid (see FIGS. 6A and 6B), set of glasses (see FIG. 7), or implantable sensor in a hermetically sealed housing. Other sensors may be located anywhere on the user's core and head, depending on the product design, convenience, and other potential user disabilities.

Depending on the intended application, in some scenarios, these sensors may also be incorporated in the surrounding structure around the person such as a car, a room, a clinic, a hospital, a bike, a ski set, etc. In one embodiment, the sensors may be non-contact sensors which use cameras, optics, infrared, wide wavelengths, ultrasound and other types of radar-like methods to obtain signals from the brain, central nervous system, peripheral nervous system, and the body.

Each of the one or more sensors may obtain one or more signals from a user. The signals obtained by the vestibular (and startling/surprise related) motion sensor 210 may include vestibular (and startling/surprise related) signals indicative of the state of the user's vestibular (and startling/surprise related) system. The vestibular (and startling/surprise related) signals may include signals propagating along the direct pathway from the vestibular (and startling/surprise related) afferents (i.e., the horizontal and vertical semicircular canals, utricular afferents, saccule fibers, etc.) to the vestibular nuclei. Notably, the signals may be present within approximately about 100 ms of the onset of unintentional motion activity. More particularly, the vestibulo-spinal reflex (VSR) may be present within approximately about 70 ms of the onset of unintentional motion activity, and the vestibulo-ocular reflex (VOR) may be observed within approximately about 60 ms of the onset of unintentional motion activity. By contrast, non-vestibular signals which propagate along the indirect pathways (from the cortical areas, cerebellum, spinal cord, and brainstem to the vestibular nuclei) may not be present until over approximately about 150 ms of the onset of unintentional motion activity. Accordingly, in contrast to prior art systems, vestibular (and startling/surprise related) signals allow for the earlier detection of unintentional motion activity. Furthermore, the vestibular (and startling/surprise related) signals may be suppressed when motion activity is intentional (such as when a person laughs, jumps, walks, etc.) and be present when motion activity is unintentional (such as when a person falls, is startled, etc.). Accordingly, the vestibular (and startling/surprise related) signals may be indicative of events. Vestibular (and startling/surprise related) signals may also be encoded by the thalamus and cortex. Accordingly, alternative embodiments of the device may obtain vestibular (and startling/surprise related) signals from vestibular (and startling/surprise related) motion sensors 210 positioned about the thalamus and cortex. The signals obtained from the remaining sensors 220A-220G may also be indicative of the user's vestibular (and startling/surprise related) and non-vestibular (and startling/surprise related) systems.

The role of the vestibular (and startling/surprise related) signal in postural stability is discussed at least in, Mierau, A., Hülsdünker, T., & Strüder, H. K. (2015). Changes in cortical activity associated with adaptive behavior during repeated balance perturbation of unpredictable timing. *Frontiers in behavioral neuroscience,* 9, Mochizuki, G., Sibley, K. M., Cheung, H. J., & McIlroy, W. E. (2009). Cortical activity prior to predictable postural instability: is there a difference between self-initiated and externally-initiated perturbations?. *Brain research,* 1279, 29-36., Mochizuki, G., Sibley, K. M., Cheung, H. J., Camilleri, J. M., & McIlroy, W. E. (2009). Generalizability of perturbation-evoked cortical potentials: independence from sensory, motor and overall postural state. *Neuroscience letters,* 451(1), 40-44., Mochizuki, G., Boe, S., Marlin, A., & McIlroy, W. E. (2010). Perturbation-evoked cortical activity reflects both the context and consequence of postural instability. *Neuroscience,* 170(2), 599-609., and Adkin, A. L., Campbell, A. D., Chua, R., & Carpenter, M. G. (2008). The influence of postural threat on the cortical response to unpredictable and predictable postural perturbations. *Neuroscience letters,* 435(2), 120-125., the contents of all of which are herein incorporated by reference. The role of vestibular (and startling/surprise related) signals in postural stability may provide additional information regarding the ability to predict unintentional motion activity.

The electrical signals obtained by each of the sensors can be processed into one or more electronic signals by one or more processors. The one or more processors can be located at each respective sensor 210, 220A-G, or at a common processing element 240. The one or more processors 240 can be organized in a processing block 235 further comprising a data repository 242 and/or a signal preprocessor 244. One or more of the electronic signals can be transmitted by each of the sensors 210, 220A-G to a pre-processing unit 244. The preprocessing unit 244 may be configured to apply signal processing techniques which enable the electronic signals to be used by the processing element 240. The signal processing techniques may include filtering, conditioning, outlier and artifact removal, amplification and the like. Alternatively the electrical or electronic signals can be transmitted directly to the processing element 240. The transmission of electrical and/or electronic signals can be wired or wireless.

The processing element 240 may include one or more processors coupled to the at least one sensor 210, 220A-G, either directly or via the pre-processing unit 244. The processing element 240 may also be coupled to a memory 241 configured to store computer readable instructions. The computer readable instructions stored on the memory 241 may cause the processing element 240 to receive the one or more signals from the at least one sensor and extract vestibular (and startling/surprise related) data from the one or more signals.

As illustrated in FIG. 5, one or more processors 240 can be electronically coupled to each of the one or more sensors 210, 220A-220G. Alternatively, the one or more processors 240 can be electronically coupled to the sensory device unit 212 comprising each of the one or more sensors 210, 220A-220G. A single sensory device unit 212 may package the one or more sensors into a single unit that can be attached to a single location on the user. An exemplary location for the sensory device unit 212 can be on the back of the user's neck. In this location, the vestibular (and startling/surprise related) motion sensor 210 can obtain the vestibular (and startling/surprise related) signal from neurological signals generated by the vestibular nuclei which are located on either side of the brain stem. In this location, the muscular sensor 220D can be used to sense movement of the trapezius and sternocleidomastoid muscles of the neck.

The one or more processors 240 can include an electronic microprocessor and can be powered by an electrical power source, such as a battery (not shown). The one or more processors can include circuit-based processes, including possible implementation as a single integrated circuit (such as an ASIC or FPGA), a multi-chip module, a single card, or a multi-card circuit pack. As would be apparent to one skilled in the art, various functions of circuit elements may also be implemented as processing blocks in a software program. Such software may be employed in, for example, a digital signal processor, micro-controller, or general-purpose computer.

The processing element 240 may extract vestibular (and startling/surprise related) data from the one or more signals. Extracting vestibular (and startling/surprise related) data may include the steps of signal conditioning, noise reduction, normalization, and outliers and artifacts removal. In one embodiment, extracting vestibular (and startling/surprise related) data may include a time window limitation. The time window limitation may be based on an understanding of the vestibular system's anatomy and physiology. In one embodiment the time window limitation may be between about 0 and 300 milliseconds. The time window limitation may enable a high signal to noise ratio because compensatory artifacts in the signal from cortical interference and other sources may appear only after 300 milliseconds of the onset of motion. In one embodiment, the processing element 240 may include software which provides a system for real time extraction of several features from the collected data. In one embodiment, the features that may be extracted in real-time from the collected data may be defined and selected off-line based on one or more pilot studies used to generate the predetermined data. The features extracted from the one or more signals may include temporal and frequency distribution moments, dynamic ranges, short and long term cross-correlations, and the like. These features may comprise the vestibular (and startling/surprise related) data. These features may be stored as vectors in one or more data sets. Each data sets may incorporate features from all the sensors. Clustering and advanced machine learning methods, including deep learning techniques (see http://deeplearning.net/tutorial/deeplearning.pdf), may be applied to the features stored in the data sets. The extraction of vestibular (and startling/surprise related) data may be done by a specialized feature extraction software module, the program code for which may be stored on the memory 241.

The computer readable instructions stored on the memory 241 may also cause the processing element 240 to determine whether the user is undergoing an event based on the extracted vestibular (and startling/surprise related) data from the one or more signals. Alternatively, in one embodiment, determining whether the user is undergoing an event may also include extracting non-vestibular (and startling/surprise related) data from the one or more signals and using both the vestibular (and startling/surprise related) and non-vestibular (and startling/surprise related) data.

The vestibular (and startling/surprise related) data extracted from the one or more signals is compared to predetermined data in order to determine whether the user is undergoing an event. Determining whether the user is undergoing an event such as a fall or a startling movement may involve comparing vestibular (and startling/surprise related) data extracted from the obtained one or more signals to predetermined data. Determining whether the user is undergoing an event may also involve comparing non-vestibular data (such as EEG/EMG/EOG signals that are non-indicative of the vestibularvestibular (and startling/surprise related) system, gyroscope, and acceleration profiles) with predetermined data.

The predetermined data may include population data and user data. The population data may be indicative of the state of each user in a population during an event or non-event. For example, the population data may include data sets which describe the profile of signals obtained from the one or more sensors from multiple users in event or non-event states. The population data may be stored on the memory 241 coupled to the processor 240. Alternatively, the population data may be stored remotely from the device and accessed by the processor via a wireless internet connection or the like.

The predetermined data may also include user data. The user data may be indicative of the state of the user's vestibular (and startling/surprise related) system during previous event or non-event states. In one embodiment, the user data may be obtained during a trial period where the user undergoes push and jump trials. During the push and jump trials the user's vestibular (and startling/surprise related) system activity before, during, and after push and jump events are recorded to determine the response of the user's vestibular (and startling/surprise related) system to intentional movements such as a jump and unintentional movements such as a push. Preliminary movement studies have illustrated suppression of vestibular (and startling/surprise related) activity in intentional movements. Preliminary movement studies have also illustrated a lack of suppression of vestibular (and startling/surprise related) activity in unintentional movements.

In addition to vestibular (and startling/surprise related) data, the predetermined data and user data may also include non-vestibular data such as acceleration and gyroscope profiles. In one embodiment, non-vestibular data such as acceleration and gyroscope profiles may be compared against predetermined data comprising non-vestibular data from the population and user in order to make a determination as to whether the user is undergoing an event such as a fall or a startling movement.

In another embodiment, the predetermined data can be used in connection with one or more classification algorithms, so that data and information extracted from the one or more signals obtained by the device can be classified as an event or non-event. The classification algorithms may be based in machine learning, pattern recognition, and clustering models. Alternatively, in one embodiment, a simple thresholding algorithm may be applied where the predetermined data is used to establish thresholds which characterize motion information as indicative of a non-event or event. In such an embodiment, the vestibular (and startling/surprise related) and/or non-vestibular (and startling/surprise related) signals processed by the one or more processors 240 may be compared to the thresholds to determine whether the user is undergoing an event or non-event. The determination of whether a user is undergoing an event may be done in substantially real-time. The system may be configured to provide continuous monitoring to a user. As the vestibular (and startling/surprise related) signals may be acquired within 150 ms of the onset of the event, the processor can make an accurate determination as to whether a movement is an event within about 50 to 200 milliseconds and transmit the signal to activate the safety device.

When the one or more processors 240 determines that a user is undergoing an event by comparing the vestibular (and startling/surprise related) data to predetermined data one or more activation signals can be transmitted from the one or more processors 240 to a safety device 250. Upon receiving the one or more activation signals, the safety device 250 can deploy. The one or more processors 240 can include software code including instructions to determine whether the user is undergoing an event, generate and transmit the activation signals, and the like.

The one or more processors 240 can optionally generate and transmit alarm activation signals configured to activate an alarm system 255 coupled to the one or more processors 240. The alarm system can be configured to provide an alert to the user, a caregiver, a medical professional and the like. For example, the alert can include a communication such as a text, message, phone call or e-mail, a loud beeping noise, a light that is triggered at a nurses' station, and the like. The alarm activation signals can be transmitted from the one or more processors 240 to the alarm system 255 in a wired or wireless method.

The one or more processors 240 can optionally transmit data and information relating to the electrical and electronic signals to one or more data storage devices or data repositories 242. The one or more processors 240 can be communicatively coupled to a data repository 242 including memory. The data repository 242 can be located with the one or more processors in the processing block 235 or the data repository 242 can be located away from the one or more processors 240 (as illustrated in FIG. 5). The communicative coupling may be wired or wireless.

The data repository 242 can be configured to collect and store the data and information including raw signals from each of the sensors 210, 220, 230 and results from the one or more processors 240. The data and information can be archived, analyzed, and communicated to third parties in order to gather data and information regarding medical conditions. In such an application of the present invention, safety device 250 can be optionally omitted.

By way of example only, data received and stored by the one or more processors 240 can be transmitted to a third party device, such as that belonging to a physician, for a Parkinson's Disease patient who is using system 200. The data received and stored by the third party device can be used to interpret whether the patient's motions are unusually rigid, perform gait analysis and/or postural stability analysis. The data and information can be used to determine whether a patient's medication dosage needs to be adjusted. For example, if the data indicates that the patient exhibits volatility and fluctuations in motor behavior over a period of time, a patient's medication dose may be adjusted. In this manner, at least one embodiment of the system can provide continuous patient monitoring. When the data and information is communicated to the patient's physician, the physician can contact the patient and tell the patient to adjust the dosage of medication. In an exemplary embodiment, the patient can be informed directly, such as, for example, through a patient-owned/operated electronic device through which the data indicates improper dosing and that the patient should either adjust the dosing or contact the patient's physician to inquire into changing the dosing prior to doing so. While the exemplary medical condition discussed above is Parkinson's Disease, those skilled in the art will recognize that system 200 can be used to indicate aberrations in the motions of a patient with other physical issues/ailments including, but not limited to, strokes, chronic dizziness, and other maladies.

In an exemplary embodiment, data and information from a single user can be stripped of all personally identifying information either prior to transmission to the data repository 242 or upon receipt at the data repository 242. The data repository 242 can store the data and information from multiple users of the system 200. The data and information can be combined to form a database for further clinical studies to better understand an illness, disease state, the effects of a pharmaceutical drug or therapy, and the like. The data may also be uploaded to a web service or the like. The combined data and information from multiple users may form, at least in part, the population data used by the device to determine whether a user is undergoing an event.

In an exemplary embodiment, a safety device 250 can be electronically coupled to the one or more processors 240 such that when it is determined that the user is undergoing an event by comparing the vestibular (and startling/surprise related) data to predetermined data an activation signal can be transmitted to the safety device 250. Safety devices can include airbags (see above with regards to FIG. 2), exoskeletons (see above with regards to FIG. 3), hip protectors (see below with regards to FIG. 8), and the like.

Examples of a safety device 250 include the wearable airbags found in U.S. Pat. Nos. 5,500,952, 7,017,195, 7,150, 048 and US. Patent Application Publication numbered 2005/0067816. These references relate to wearable airbag clothes coupled with a non-vestibular sensor to sense the movement of a person wearing the wearable airbag clothes.

The safety device 250 (i.e., airbag) can be made of a tear-resistant material such as nylon with polyurethane coating. Other materials can be used as well without departing from the scope of the invention. The airbag cushion can include an inner cavity that is sized and shaped so that during inflation the airbag is quickly filled with gas, but during impact the gas outflow from the airbag is delayed.

In one implementation, the inner cavity of the airbag cushion can be sectioned into a plurality of inner sections/chambers. For example, each of the inner sections can be connected to the neighboring sections with one or more air passages. Each of the inner sections can comprise multiple inner chambers so that the smaller chambers can inflate faster and can provide enough protection to body parts during impact. By sectioning the airbag, smaller areas will be fully inflated faster to quickly provide enough protection for the user. Sectional airbag design is advantageous in that it will delay the air outflow when a user falls on top of the airbag.

As discussed in US 2016/0067123 (the contents of which are incorporated herein by reference), all of the inner sections/chambers of an airbag can be separated and each of such chambers can inflate separately and independently from each other, aiding in slowing egress of gas flow. For example, each of the inner section can be connected to the air movement system via a separate valve. The air movement system can comprise a manifold with a number of ports, each of the ports connected to a separate inner section of the cushion. In such embodiment, each of the inner sections can be deployed automatically at the same time. The airbag system can comprise one or more vent-valves to provide slow release of the airbag cushion upon a fall impact.

Other embodiments of an airbag may comprise a pneumatic airbag system, including a pneumatic sub-system. The pneumatic sub-system may also include a gas canister connected to a gas pressure gage and a gas discharge valve connected to a gas outlet. The gas outlet may be connected to a pneumatic tubule, which is split by means of a manifold, from which a pneumatic tubule goes to each gas intake valve of each one of the airbags.

The vestibular (and startling/surprise related) motion sensor 210 of system 200 can be used in addition to or as a substitute for the brain signal sensor 100. Accordingly, similar to the training methods discussed above with regards to system 100, system 200 can also utilize training methods to establish appropriate thresholds for the one or more signals obtained from the vestibular (and startling/surprise related) motion sensors.

Figure 6A:
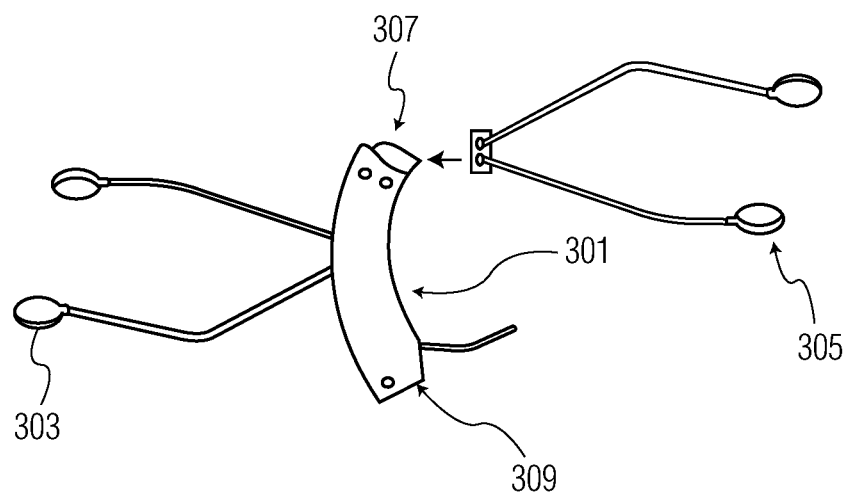
FIG. 6A shows a vestibular (and startling/surprise related) motion sensor in connection with a hearing aid-like device located behind a user's ear according to an exemplary embodiment of the present invention.

FIG. 6A illustrates an example of a fall and collision detection and injury mitigation system 300 using a vestibular (and startling/surprise related) motion sensor 303 which is coupled to a muscular sensor 305 and a movement sensor 309 according to an exemplary embodiment of the present invention as discussed with regards to FIG. 5. As illustrated, the sensors 303, 305, and 309 can be embedded within a hearing aid 301 device configured to be positioned behind a user's ear. Accordingly, in the depicted example, the vestibular (and startling/surprise related) motion sensor 303 is non-invasive. The vestibular (and startling/surprise related) motion sensor 303 can include EEG electrodes configured to be positioned across the scalp so as to pick up cortical waveforms. The EEG electrodes may also be placed against the skin external to the ear canal. In one embodiment, the EEG electrodes may be placed proximate other muscle groups and/or places on the human body which may be involved in motion. The fall and collision detection and injury mitigation system 300 can optionally include a muscular sensor 305 which includes EMG electrodes. The muscular sensor 305 can be coupled to the fall and collision detection and injury mitigation system 300 at a socket 307. The fall and collision detection and injury mitigation system 300 can also optionally include a movement sensor 309 further including one or more accelerometers. The movement sensors 309 may be configured to extract signals which propagate due to the physical transduction phenomena (relative acceleration, velocity, jerk, pressure, voltage etc.). Muscular sensors may exploit the cellular action potentials which propagate along the skin's surface.

Figure 6B:
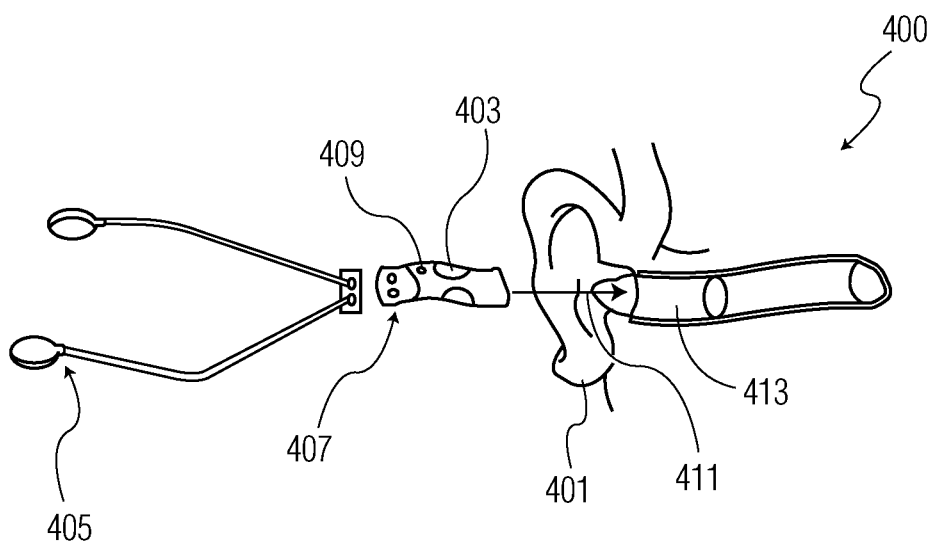
FIG. 6B shows a vestibular (and startling/surprise related) motion sensor in connection with a hearing aid-like device inserted in a user's ear according to another exemplary embodiment of the present invention.

FIG. 6B illustrates an alternative example of a fall and collision detection and injury mitigation system 400 also using a vestibular (and startling/surprise related) motion sensor 403 which is coupled to a muscular sensor 405 and a movement sensor 409 according to an exemplary embodiment of the present invention as discussed with regards to FIG. 5. As illustrated, the hearing aid-like device 401 can be inserted in direction 411 into a user's ear canal 413. Accordingly, in the depicted example, the vestibular (and startling/surprise related) motion sensor 403 is partially invasive. The vestibular (and startling/surprise related) motion sensor 403 further includes EEG electrodes which are positioned within the ear canal and can obtain vestibular signals. Advantageously, the placement of the EEG electrodes within the ear canal allows for the obtainment of cleaner (i.e., less noisy) signals. The fall and collision detection and injury mitigation system 400 can optionally include a muscular sensor 405 which includes EMG electrodes. The muscular sensor 405 can be coupled to the fall and collision detection and injury mitigation system 400 at a socket 407. The fall and collision detection and injury mitigation system 400 can also optionally include a movement sensor 409 further including one or more accelerometers.

Figure 7:
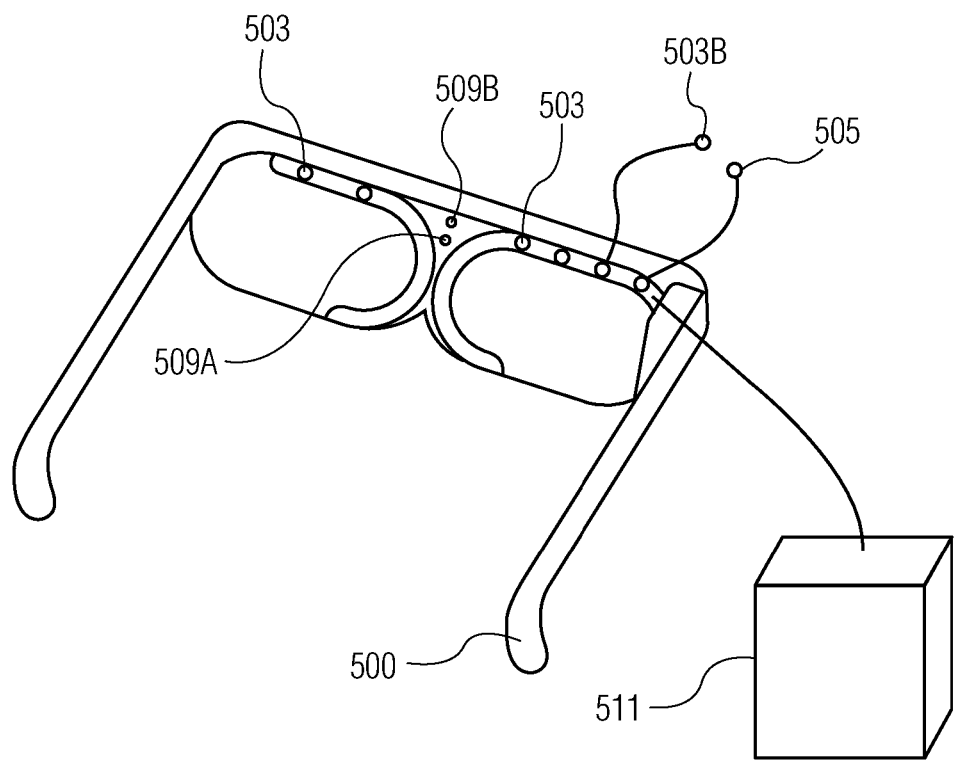
FIG. 7 shows a vestibular (and startling/surprise related) motion sensor in connection with a set of glasses according to an exemplary embodiment of the present invention.

FIG. 7 illustrates an alternative example of a fall and collision detection and injury mitigation system 500 also using a vestibular (and startling/surprise related) motion sensor 503 which is coupled to a muscular sensor 505 and a movement sensor 509 according to an exemplary embodiment of the present invention as discussed with regards to FIG. 5. As illustrated, the glasses-like device 501 can rest on the bridge of a user's nose and ears. Accordingly, in the depicted example, the vestibular (and startling/surprise related) motion sensor 503 is non-invasive. The vestibular (and startling/surprise related) motion sensor 503 can include eye-tracking cameras configured to obtain information regarding the VOR. The vestibular (and startling/surprise related) motion sensor 503 can also include one or more electrodes configured to receive EEG 503B and/or EMG 505 signals. The electrodes configured to receive EMG 505 can also receive muscular information. The one or more electrodes configured to receive EEG 503B and/or EMG 505 signals can be positioned on the user's temple. The fall and collision detection and injury mitigation system 500 can also optionally include one or more movement sensors including one or more accelerometers 509A and gyroscopes 509B. As depicted the device 501 can transmit data and information wired or wirelessly to a controller 511 including the processing block 235 (discussed above). Alternatively the processing block 235 can be mounted to the frame of the device 501.

Figure 8:
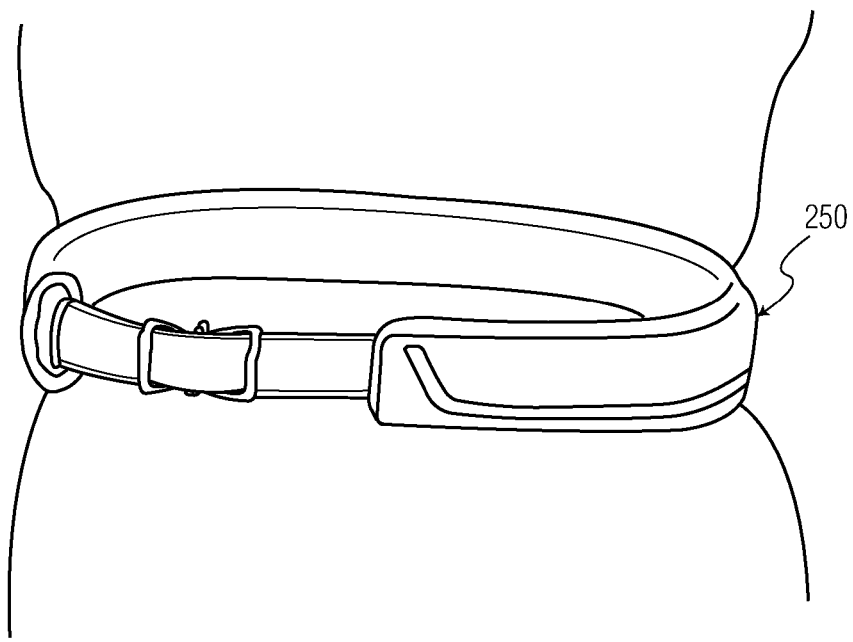
FIG. 8 shows an exemplary wearable safety device for use with the vestibular (and startling/surprise related) motion sensors according to an exemplary embodiment of the present invention.

FIG. 8 shows an exemplary wearable safety device 250 for use with the vestibular (and startling/surprise related) motion sensors 210, 303, 403, 503 according to an exemplary embodiment of the present invention. As depicted, the safety device 250 is a low profile waist belt. The safety device 250 can be electronically coupled to controller 511 and/or processing block 235 such that when it is determined that data extracted from signals obtained from the user indicate an event the controller 140 and/or processing block 235 can transmit an electronic signal to the safety device 250 in order to activate the safety device 250. The safety device 250 can be configured to protect the hip area, an area known to be prone to injury in elderly patients. Additionally the safety device 250 can be camouflaged by or worn under everyday clothing thereby reducing the aesthetically unpleasing factors associated with conventional safety devices. The vestibular (and startling/surprise related) motion sensors also reduce the aesthetically unpleasing factors associated with conventional devices by taking advantage of the latest wearable devices technology and incorporating accepted platforms of eye trackers and hearing aids technology in an ergonomic and user friendly way.

EXAMPLES

In one example, user data obtained by experiments was used as predetermined data. The user data was transmitted to and/or stored in a data repository. In the example user data was gathered from experiments using push and jump trials. In push and jump trials EEG, EMG, linear and angular acceleration data were obtained from a subject when the subject was pushed or encouraged to fall from a bench at similar acceleration profiles over multiple trials.

The push and jump trials utilized a device with 24 bit resolution, 5000 Hz sampling rate, wide band DC-3500 Hz, a large dynamic range of +/−430 mV, AC and DC measurement modes that were switchable channel by channel, 40-channel amplifier having 32 EEG and 8 bipolar channels. The device also included a 2D accelerometer with a range of +/−6 g and a 1D gyroscope.

The device obtained vestibular and other signals through EEG electrodes. Passive EEG electrodes were present on a head cap. The electrodes were placed on subject's head in accordance with the international 10-10 system in which electrodes are spaced apart by approximately 10% of the total front-back or right-left distance of the skull. Alternatively the higher resolution international 10-5 system or the lower resolution international 10-20 system may be used. Any electrode placement that results in obtaining vestibular and other signals may be used. In the example, a reference electrode was placed between the left mastoid and the O1 electrode from the international 10-10 system. A ground electrode was placed between the right mastoid and the O2 electrode from the international 10-10 system. Alternatively, the reference electrode may have been attached to one earlobe and the ground electrode may have been attached to the mastoid on the same side of the head. In yet another alternative, the reference electrode may have attached to one mastoid and the ground electrode may have attached to another.

In the example EMG sensors were symmetrically placed about other regions of interest on the subject including under the eye, on the back of the neck, and on the shoulder.

In the example a 2D accelerometer and 1D gyroscope were placed along the lower back area of the subject. The 2D accelerometer measured movement along the up and down axis parallel to the subject's spine, and the forward and backward movement of the subject. The 1D gyroscope aided in measuring the subjects's rotation about the axis parallel to the subject's spine.

During the push and jump trials the user's vestibular (and startling/surprise related) system activity before, during, and after push and jump events were recorded to determine the response of the user's vestibular (and startling/surprise related) system to intentional movements such as a jump and unintentional movements such as a push.

During each push and jump trial a subject stood on the bench with their eyes closed. The subject was connected to a harness, wore a jacket, or other safety equipment. The subject was connected to the device and in particular one or more EEG electrodes, one or more EMG electrodes, one or more accelerometers, and/or one or more gyrometers as described above. The subject was pushed forwards or backwards without notification, causing the subject to fall. The time at which the subject was pushed was recorded. The subject was then asked to stand on the bench with their eyes closed again. The subject was then asked to mimic the fall event.

Data from multiple channels including for data related to EEG sensors, EMG sensors, linear acceleration and angular acceleration was obtained, digitized and sampled. The data was sampled at 5000 Hz and received from 64 channels.

Figure 9:
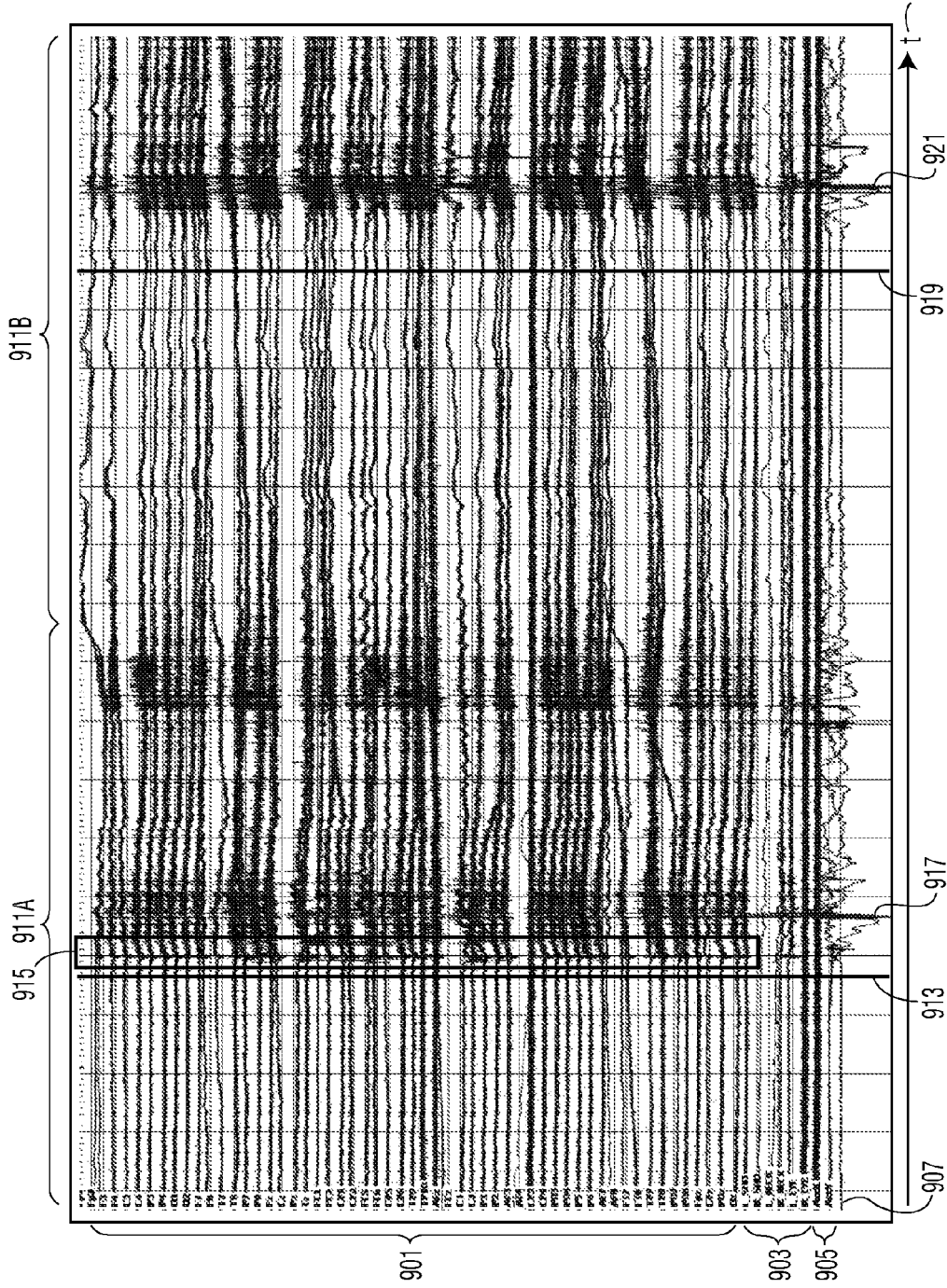
FIG. 9 shows example data obtained from vestibular (and startling/surprise related) sensors used in connection with an exemplary embodiment of the present invention.

A composite image from the push and jump trials is depicted in FIG. 9. As illustrated in FIG. 9 waveforms from push and jump trials were viewed within a graphical user interface (GUI) 900 of a computer software configured to display data related to the device. Waveforms representative of EEG data 901, waveforms representative of EMG data 903, waveforms representative of acceleration data 905, waveforms representative of gyroscope data 907 were shown over time along a time axis 909. Waveforms associated with a pushing event were found in the region marked as '911A.' Waveforms associated with an intended jumping event were found in the region marked '911B.' Shortly after a push was initiated 913 a sharp cluster of spikes 915 was observed in waveforms indicative of EEG data. Afterwards a drastic change in acceleration was observed 917 in the waveforms representative of accelerometer and gyroscope data. The drastic change in acceleration may be attributed to movement, falling, landing, etc. By contrast, when the subject initiates an intentional movement such as a jump 919 there is no sharp cluster of spikes observed prior to the observed drastic change in acceleration 921.

The cluster of spikes observed prior to the drastic change in acceleration when the push is initiated may be indicative of vestibular (and startling/surprise related) activity. Accordingly, the push and jump trials indicate that vestibular activity (as illustrated by the cluster of spikes) may be suppressed in intentional motion. Accordingly vestibular (and startling/surprise related) activity may be indicative of falling motion.

In summary FIG. 9 shows example data obtained from vestibular (and startling/surprise related) sensors used in connection with an exemplary embodiment of the present invention. In particular the example data indicates a suppression of vestibular (and startling/surprise related) activity in intentional movements. The example data also indicates a lack of suppression of vestibular (and startling/surprise related) activity in unintentional movements.

It will be further understood that, as for example many other safety device activation command algorithms may be implemented based on public domain techniques such as machine learning, adaptive control, sensors fusion, signal processing etc., various changes in the details, materials, and arrangements of the parts which have been described and illustrated in order to explain the nature of this invention may be made by those skilled in the art without departing from the scope of the invention as expressed in the following claims.

The invention claimed is:

1. A system comprising:
at least one sensor configured to obtain one or more signals from a user, wherein the at least one sensor further comprises a vestibular sensor specially configured to obtain vestibular signals indicative of propagation of electrical activity between one or more of vestibular afferents and vestibular nuclei;
at least one processor coupled to a memory storing computer readable instructions, the at least one processor electronically coupled to the at least one sensor, the computer readable instructions causing the processor to:

receive the one or more signals from the at least one sensor, wherein the one or more signals further comprises at least one vestibular signal, extract vestibular data from the one or more signals, wherein the vestibular data is indicative of a state of the user's vestibular system, determine whether the user is undergoing an event by comparing the vestibular data to predetermined data, and transmit an activation signal to a safety device when it is determined that the user is undergoing the event; and the safety device being configured to deploy when the activation signal is received from the at least one processor.

2. The system of claim 1, wherein the event is at least one of a fall and a startling movement.

3. The system of claim 1, wherein the vestibular sensor further comprises at least one of:
at least one dedicated vestibular electroencephalogram (EEG) sensor, and
at least one dedicated vestibular electromyography (EMG) sensor, each of the at least one dedicated vestibular EEG sensor and at least one dedicated EMG sensor positioned about one or more body parts of the user participating in motion stability.

4. The system of claim 1, wherein the at least one sensor comprises one or more of an accelerometer, a gyroscope, an electroencephalogram (EEG) sensor, an electromyograph (EMG) sensor, a near- infrared spectroscopy (NIRS) sensor, and an eye-tracker camera.

5. The system of claim 1, wherein at least one of the one or more sensors and the at least one processor are located on a wearable device.

6. The system of claim 4, wherein the wearable device resembles at least one of glasses and a hearing aid.

7. The system of claim 1, wherein the at least one processor is further configured to transmit the vestibular data to a data repository, the data repository further configured to store at least a portion of the received vestibular data.

8. The system of claim 1, wherein the safety device further comprises at least one of an exoskeleton and a deployable airbag.

9. The system of claim 1, wherein the predetermined data further comprises at least one of population data and user data,
wherein the population data is indicative of the state of the vestibular system across a population during previous events, and
wherein the user data is indicative of the state of the user's vestibular system during previous events.

10. The system of claim 1, wherein the predetermined data is adjusted by a learning adaptive algorithm.

11. The system of claim 1, wherein extracting vestibular data further comprises applying at least one of signal conditioning, noise reduction, normalization, extraction of features to the one or more signals.

12. A method comprising:
obtaining, by at least one sensor, one or more signals from a user, wherein the at least one sensor further comprises a vestibular sensor specially configured to obtain vestibular signals and the one or more signals further comprises at least one vestibular signal indicative of propagation of electrical activity between one or more of vestibular afferents and vestibular nuclei;

transmitting, by the at least one sensor, the one or more signals to at least one processor, wherein the at least one processor is coupled to a memory storing computer readable instructions and the at least one processor is electronically coupled to the at least one sensor;

receiving, by the at least one processor, the one or more signals from the at least one sensor;

extracting, by the at least one processor, vestibular data from the one or more signals, wherein the vestibular data is indicative of a state of the user's vestibular system;

determining, by the at least one processor, whether the user is undergoing an event by comparing the vestibular data to predetermined data;

transmitting, by the at least one processor, an activation signal to a safety device when it is determined that the user is undergoing the event; and deploying the safety device when the safety device receives the activation signal from the at least one processor.

13. The method of claim 12, wherein the event is at least one of a fall.

14. The method of claim 12, wherein the vestibular sensor further comprises at least one of:
at least one dedicated vestibular electroencephalogram (EEG) sensor, and
at least one dedicated vestibular electromyography (EMG) sensor, each of the at least one dedicated vestibular EEG sensor and at least one dedicated EMG sensor positioned about one or more body parts of the user participating in motion stability.

15. The method of claim 12, wherein the at least one sensor comprises one or more of an accelerometer, a gyroscope, an electroencephalogram (EEG) sensor, an electromyograph (EMG) sensor, a near- infrared spectroscopy (NIRS) sensor, and an eye-tracker camera.

16. The method of claim 12, wherein at least one of the one or more sensors and the at least one processor are located on a wearable device.

17. The method of claim 16, wherein the wearable device resembles at least one of glasses and a hearing aid.

18. The method of claim 12, further comprising:
transmitting, by the at least one processor, the vestibular data to a data repository, wherein the data repository further configured to store at least a portion of the received vestibular data.

19. The method of claim 12, wherein the safety device further comprises at least one of an exoskeleton and a deployable airbag.

20. The method of claim 12, wherein the predetermined data further comprises at least one of population data and user data,
wherein the population data is indicative of the state of the vestibular system across a population during previous events, and
wherein the user data is indicative of the state of the user's vestibular system during previous events.

21. The method of claim 12, wherein the predetermined data is adjusted by a learning adaptive algorithm.

22. The method of claim 12, wherein extracting vestibular data further comprises:
applying at least one of signal conditioning, noise reduction, normalization, extraction of features to the one or more signals.

* * * * *